United States Patent [19]

Gianni

[11] Patent Number: 5,649,904

[45] Date of Patent: Jul. 22, 1997

[54] METHOD OF TREATING CANCER WITH A FULLY MYELOABLATIVE REGIMEN OF CHEMOTHERAPY, RADIATION OR BOTH

[75] Inventor: Alessandro M. Gianni, Milan, Italy

[73] Assignees: Sandoz Ltd., Basle, Switzerland; Instituto Nazionale Per Lo Studio E La Cura Dei Tumori, Milan, Italy

[21] Appl. No.: 452,461

[22] Filed: May 26, 1995

Related U.S. Application Data

[63] Continuation of Ser. No. 303,783, Sep. 9, 1994, abandoned, which is a continuation of Ser. No. 158,662, Nov. 29, 1993, abandoned, which is a continuation of Ser. No. 7,459, Jan. 22, 1993, abandoned, which is a continuation of Ser. No. 910,479, Jul. 8, 1992, abandoned, which is a continuation of Ser. No. 367,657, Jun. 19, 1989, abandoned, which is a continuation-in-part of Ser. No. 289,169, Dec. 23, 1988, abandoned.

[30] Foreign Application Priority Data

Oct. 7, 1988 [JP] Japan .................................... 63-254681

[51] Int. Cl.$^6$ .................................................. A61M 37/00
[52] U.S. Cl. .......................... 604/4; 128/898; 530/351; 604/49
[58] Field of Search .......................... 604/4–6, 49; 514/2, 514/12, 15, 17, 21; 128/598; 424/1.1; 530/351; 600/1–3

[56] References Cited

U.S. PATENT DOCUMENTS

| | | | |
|---|---|---|---|
| 4,778,879 | 10/1988 | Mertelsmann | 530/351 |
| 4,863,902 | 9/1989 | Amagase | 514/12 |
| 4,898,818 | 2/1990 | Nakai | 435/69.1 |
| 4,908,433 | 3/1990 | Mertelsmann | 530/351 |
| 5,008,374 | 4/1991 | Nakai | 530/351 |

OTHER PUBLICATIONS

Brandt et al., N. Engl. J. Med. 318, 869–876 (1988). (Apr. 07).
Gabrilove et al., N. Engl. J. Med. 318, 1414–1422 (1988). (Jun. 02).
Gianni et al., Hematolog. Oncol. 7, 139–148 (1989).
Gianni et al., Lancet 1989, 580–584. (Sep. 09).
Gianni et al., Bone Marrow Transplant. 6, 143–145 (1990).
Socinski et al., Lancet 1988, 1194–1198 (May 28).
Tilly et al., Leukemia Research 10, 353–356 (1986).
To et al., Brit. J. Haematol. 58, 399–410 (1984).
Nakai et al. "The Therapeutic Potential of IL–1B in the Treatment of Chemotherapy Radiation Induced Myelosuppresion in Tumor Therapy" Biotherapy, vol. 1 #4, 1989, pp. (339–354–abstract only).
Steward et al. "Recombinant Human Granulocyte Macrophage Stimulating Factor with GM–CSF Given as Daily Short Infusions: a Phase One Dose Toxicity Stud" British Jrnl. of Cancer, vol. 59 #1, 11989 (abstract only).
Mertelsmann et al. "Prevention of Chemically Induced Neutropenia and Associated Morbidity . . . GM–CSF" 18 Annual Mtg. of American Ass. for Cancer Research, May 24–27, 1989.
Ganser et al. "Chemical Effects of Recombinant Human 16–3" American Jrnl of Clinical Oncology, vol. 14, suppl., 1991, pp. 951–956 (abstract only).

Primary Examiner—Corrine M. McDermott
Assistant Examiner—Chalin Smith
Attorney, Agent, or Firm—Robert S. Honor; Melvyn M. Kassenoff

[57] ABSTRACT

The use, in sequence, of a cytotoxic, but stem cell sparing, agent and granulocyte-macrophage colony stimulating factor as a means to harvest very high numbers of multipotential haemopoietic precursor cells and in reducing the period of myeloid recovery after high dose chemo- or radiotherapy of cancer.

24 Claims, 5 Drawing Sheets

Days from stem cell transplantation

METHOD OF TREATING CANCER WITH A FULLY MYELOABLATIVE REGIMEN OF CHEMOTHERAPY, RADIATION OR BOTH

This is a continuation of application Ser. No. 08/303,783, filed Sep. 9, 1994 and now abandoned, which is a continuation of application Ser. No. 08/158,662, filed Nov. 29, 1993 and now abandoned, which is a continuation of application Ser. No. 08/007,459, filed Jan. 22, 1993 and now abandoned, which is a continuation of application Ser. No. 07/910,479, filed Jul. 8, 1992 and now abandoned, which is a continuation of application Ser. No. 07/367,657, filed Jun. 19, 1989 and now abandoned, which is a continuation-in-part of application Ser. No. 07/289,169, filed Dec. 23, 1988.

The present invention relates to a new application, in particular a new pharmaceutical application, for a haemopoietic progenitor cell stimulating factor (herein HPSF) which has a component of activity of a colony stimulating factor (hence herein also CSF), and which is especially represented by the cytokine granulocyte-macrophage colony stimulating factor (GM-CSF). More specifically it pertains to the use, in sequence, of a cytotoxic, but stem cell sparing, agent and an HPSF. Suitable HPSF compounds other than GM-CSF include granulocyte colony stimulating factor (G-CSF) and interleukin-3 (IL-3).

Granulocyte-macrophage colony stimulating factor is known and has been described, together with processes for its production by recombinant DNA methods, for example in European Patent Publication 188,479 and equivalents worldwide.

Similarly, G-CSF, IL-3 and other HPSF compounds are also known and their preparation is described in the literature. The purification of G-CSF is described in European Patent 169,566, and its preparation by recombinant DNA technology is given in EPA 215,126; while the recombinant preparation of IL-3 is described and claimed in PCT application WO 88/00598. As described in EPA 188,479, GM-CSF is known from various animal sources. The present invention, however, is particularly concerned with primate and more particularly with human GM-CSF and other HPSFs.

The GM-CSF used in the present invention may be prepared by any of the means known in the art. For example, as described in the above mentioned EPA 188,479, it may be produced as the result of recombinant DNA expression. It and other known HPSFs may also be isolated from natural sources or produced synthetically.

It is known that GM-CSF is a factor which is required for the survival, proliferation and differentiation of myeloid progenitor cells which are committed to form mature granulocytes and macrophages (CFU-GMs). G-CSF similarly acts on myeloid progenitor cells committed to form mature granulocytes. Each is useful in the treatment of myelosuppression caused by chemotherapeutic or irradiation treatment of cancer. Under such circumstances the HPSF is administered to a patient, treated with chemo- or irradiation therapy, after the re-infusion of previously removed bone marrow (autologous bone marrow) in order to stimulate the proliferation and differentiation of the myeloid progenitor cells found in the bone marrow. GM-CSF may also be administered for 3–5 days before the removal of bone marrow for later re-infusion.

The cytotoxic, but stem cell sparing, agent is, for example cyclophosphamide [N,N-Bis(2-chloroethyl) tetrahydro-2H-1,3,2-oxazophosphorin2-amine-2-oxide)], a known compound whose preparation was first described by Arnold et al (Naturwiss 45 (1957) 64). Other suitable such agents include etoposide (VP-16), whose preparation is described by Keller-Justen et al in J Med Chem 14 (1971) 936.

It is known that a dose of a cytotoxic agent, such as cyclophosphamide, has the effect of stopping proliferation of bone marrow cells. However, the cytotoxic effect upon the cells which normally regulate proliferation is longer lasting, so that upon recovery from the treatment, bone marrow proliferation is rapid and uncontrolled. It has therefore been proposed to treat patients with a cytotoxic, but stem cell sparing, agent such as cyclophosphamide 14 days before removal of bone marrow for re-infusion following chemo- or radio-therapy, so that the bone marrow will be in an actively proliferating state when removed.

It has now been found that when the bone marrow is in this actively proliferating state, many progenitor stem cells appear in the peripheral blood circulation. The differentiation of these circulating stem cells may be stimulated by treatment with HPSF in the period following treatment with the cytotoxic agent. It has further been found that if, after cytotoxic agent/HPSF treatment, peripheral blood is removed at the same time as bone marrow, and this blood, or leukocytes obtained from this blood, are re-infused together with the bone marrow, myeloid recovery is considerably more rapid than is normally the case.

DETAILED DESCRIPTION

The present invention provides a method of treatment of a patient requiring high-dose chemo- or radiotherapy for cancer, with rescue by autologous bone marrow transplantation comprising the steps of:

a) administering a high dose of a cytotoxic, but stem cell sparing, agent, b) administering a haemopoietic progenitor cell stimulating effective amount of a HPSF, c) when the bone marrow is in an actively proliferating state and precursor stem cells are present in the peripheral blood, removing bone marrow and a volume of peripheral blood or leukocytes obtained therefrom d) administering a fully myeloablative regimen of chemo- or radiotherapy e) re-infusing bone marrow and peripheral blood, or leukocytes obtained therefrom;

and, optionally, f) again administering a HPSF, for a period of time until myeloid recovery has occurred.

Preferred embodiments of the method are those (1) wherein the HPSF employed in Step b) is GM-CSF, (2) wherein the HPSF employed in Step b) is IL-3, (3) of (1) wherein GM-CSF is administered by infusion 24 hours subsequent to the administration of the cytotoxic but stem cell-sparing agent, (4) of (3) wherein the removal of bone marrow and a volume of peripheral blood, or leukocytes obtained therefrom, is effected 12–21 days subsequent to the administration of the cytotoxic but stem cell-sparing agent, (5) of (4) wherein said removal occurs when the leukocytes exceed 1,000/μL and the platelets exceed 100,000/μL, (6) wherein the fully myeloablative regimen of Step d) involves total body radiation plus melphalan, (7) of (6) wherein the reinfusion of Step e) occurs 3–24 hours after Step d), (8) wherin the cytotoxic but stem cell-sparing agent is cyclophosphamide, (9) of (8) wherein the cyclophosphamide is administered at a dosage of 6–7 g/m$^2$, (10) wherein in Step b) the HPSF is administered as a continuous infusion, (11) of (10) wherein GM-CSF is administered at a dosage of 6–24 μg/per/day, and (12) of (11) wherein the dosage is 8 μg/Kg/day.

In a preferred embodiment of the present invention the cytotoxic, but stem cell sparing, agent is cyclophosphamide, and the HPSF is GM-CSF or IL-3.

It is surprisingly found that if bone marrow cells are supplemented with circulating stem cells, the myeloid recovery, post chemo or radio therapy, occurs after an average of 10 days instead of 14 days or more. Although not yet fully understood, it is believed that the HPSF acts on the progenitor cells in the peripheral blood, stimulating them to differentiate, such that 12–21 days after treatment with the cytotoxic, but stem cell sparing, agent, the committed precursors (e.g. CFU-GM's) are present in extremely high numbers. These CFU-GM's give rise, in in vitro culture, to mature progeny after 7–14 days. The re-infusion of this cytotoxic agent/HPSF treated peripheral blood results in the extremely rapid recovery period.

The present invention also envisages the use of a HPSF infusion after peripheral blood and bone marrow transplantation. As CFU-GMs are the main target of GM-CSF and G-CSF, it is anticipated that a further acceleration in the circulating granulocyte appearance would result from such a post-transplant infusion. Such activity of the HPSF on infused CFU-GMs is expected to prevent the circulating granulocytes from falling below the safety level of 100–500/μl, in particular when short (one-day) myeloablative regimens (i.e. melphalan alone) are used instead of the melphalan-total body irradiation combination which lasts for four days. This result is not expected to occur after infusion of bone marrow alone, as the precursors found in the bone marrow are predominantly early progenitors which have a longer maturation time.

The use of HPSF according to the present invention is particularly suitable after the chemo- or radio-therapy of refractory cancers, i.e. in those patients who have been through the normal cancer treatment programs and whose cancer was not eliminated thereby. It is envisaged that such use may be performed after treatment of solid tumors, i.e. breast cancer, lymphomas and leukaemia.

In step a), with cyclophosphamide as the cytotoxic agent, the cyclophosphamide is suitably administered in 4–5 injections, at dosages of 1.4 g/m$^2$ (final dose 6–7 g/m$^2$).

In step b), the HPSF is suitably administered as a continuous intravenous infusion for 10 to 14 days. Dosages for GM-CSF will, for example, range between 6 and 24 μg/Kg/day and preferably 8 μg/Kg/day. A subcutaneous route of infusion may be equally suitable. Administration may be 3 hours to 10 days after step a).

In step c), peripheral blood leukocytes are preferably removed by leukapheresis using a continuous flow blood cell separator (IBM 2997 or the like). The circulating stem cells are preferably harvested when the leukocytes exceed 1000/μl and the platelets exceed 100,000/μl. A total of 2 to 4 leukaphereses are performed during the early recovery phase following cyclophosphamide and HPSF infusion (usually between day 14 and day 21 post-cyclophosphamide). The total blood volume processed per run is approximately 5–10 litres at a flow rate of 35–70 ml/min.

The chemo- or radiotherapy given in step d) may be any standard or experimental regime, for example TBI 12.5 Gy plus melphalan 160 mg/m$^2$. After 1–3 hours the bone marrow plus leukocytes is re-infused (step e). Suitably the same course of GM-CSF treatment is used in step f) as in step b) (see FIG. 5).

According to a further aspect of the invention, no bone marrow is taken and myeloid recovery is achieved only by re-infusion of leukocytes from cyclophosphamide/HPSF treated peripheral blood. It is found that GM-CSF-exposed circulating mononuclear cells are highly enriched in lymphoblast-like cells giving rise in vitro to immature, multi-lineage colonies (CFU-GEMM). Thus, the present invention also provides a method of treatment of a patient requiring high dose chemotherapy or radiotherapy for cancer with rescue by leukocyte infusion comprising the steps of:

a) administering a high dose of a cytotoxic but stem cell-sparing agent, b) administering a haemopoietic progenitor cell stimulating effective amount of a HPSF, c) when precursor stem cells are present in the peripheral blood, removing a volume of peripheral blood or leukocytes obtained therefrom, d) administering a fully meyeloablative regimen of chemotherapy or radiotherapy, e) reinfusing peripheral blood or leukocytes obtained therefrom, and, optionally, f) administering a HPSF for a period of time until myeloid recovery has occurred.

GM-CSF and IL-3 are the preferred HPSFs for this method.

The above disclosure generally describes the present invention. A more complete understanding can be obtained by reference to the following specific examples which are provided herein for purposes of illustration only and are not intended to limit the scope of the invention.

EXAMPLE 1

To demonstrate the effects of cyclophosphamide and GM-CSF on myeloid recovery a comparison was performed between 14 control and 5 test patients. Five male and 9 female patients with an average age of 41.5 (range 22–55), of whom 4 had high grade, poor-prognosis non-Hodgkin's lymphoma, 7 had inflammatory breast cancer and 3 had small cell lung cancer, were used as controls and one 1 male and 4 females with an average age of 45 (range 39–53), of whom 1 had high grade non-Hodgkin's lymphoma and 4 had inflammatory breast cancer, were used as test patients.

All 19 patients were subjected to the same high dose chemotherapy programme, consisting of the sequential administration of:

a) cyclophosphamide (7 g/m$^2$) on day 0;

b) vincristine (1.4 mg/m$^2$), methotrexate (8 g/m$^2$) plus leucovorin rescue, cisplatin (120 mg/m$^2$) on days +21–25; and c) total body irradiation (12.5 Gy total) plus melphalan (120–180 mg/m$^2$) on days +42–45 or melphalan alone (200 mg/m$^2$) for inflammatory breast cancer patients.

In the 5 test patients, GM-CSF was given, starting 24 hours after cyclophosphamide infusion, as a continuous infusion via a central catheter, at 8 µg/Kg/day for 14 days in 3 patients and for 10 days in 2 patients.

Bone marrow with peripheral blood was returned the day after melphalan infusion.

Bone marrow procurement and leukapheresis are performed by standard techniques and stem cells and bone marrow cells are brought to the temperature of liquid nitrogen using controlled freezing techniques.

Blood samples were obtained prior to treatment and every 2–3 days following cyclophosphamide infusion. Details of the techniques for determination of CFU-GM are described in Lanfrancone et al, J CELL PHYSIOL 122 (1985) 7.

Haematological toxicity of high dose cyclophosphamide and effect of GM-CSF

Figure 1:
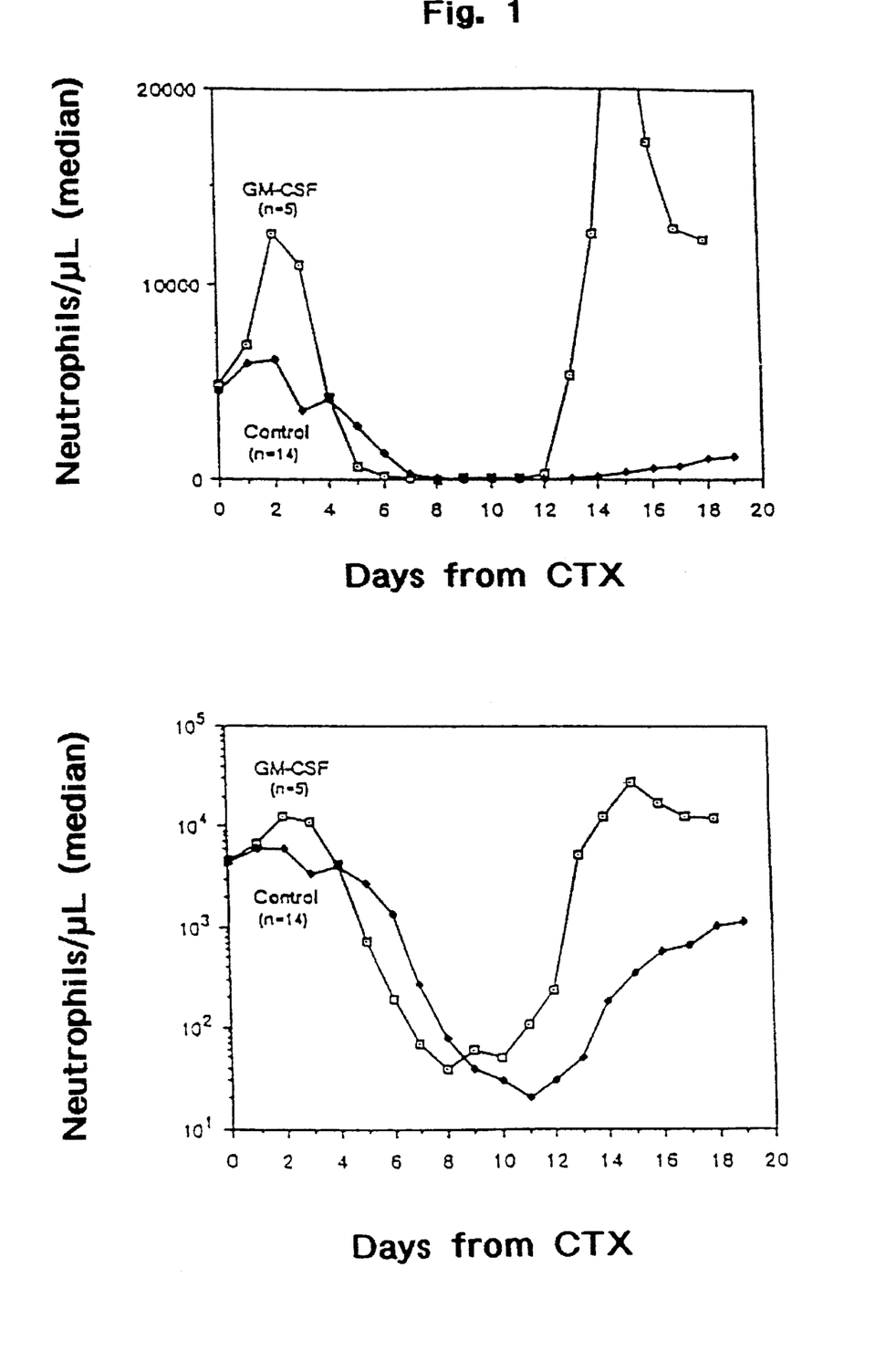
FIG. 1: granulocyte numbers (median values) following high-dose cyclophosphamide (7 g/m$^2$ on day 0) in 14 control patients (□) and in 5 patients treated with GM-CSF (♦) (8 µg/Kg/day from day 1 to day 10 or day 14). Upper panel: linear scale; lower panel: log scale.

The haematological toxicity results may be seen in FIG. 1, wherein (□) signifies the control and (♦) signifies the test regime;

Control: severe leukopenia (<500 neutrophils/µl) occurred by day eight. The recovery of neutrophils to >100/µl was achieved in 17–24 days (average 18), and to >2500/µl in 19–28 days (average 21.5).

Figure 2:
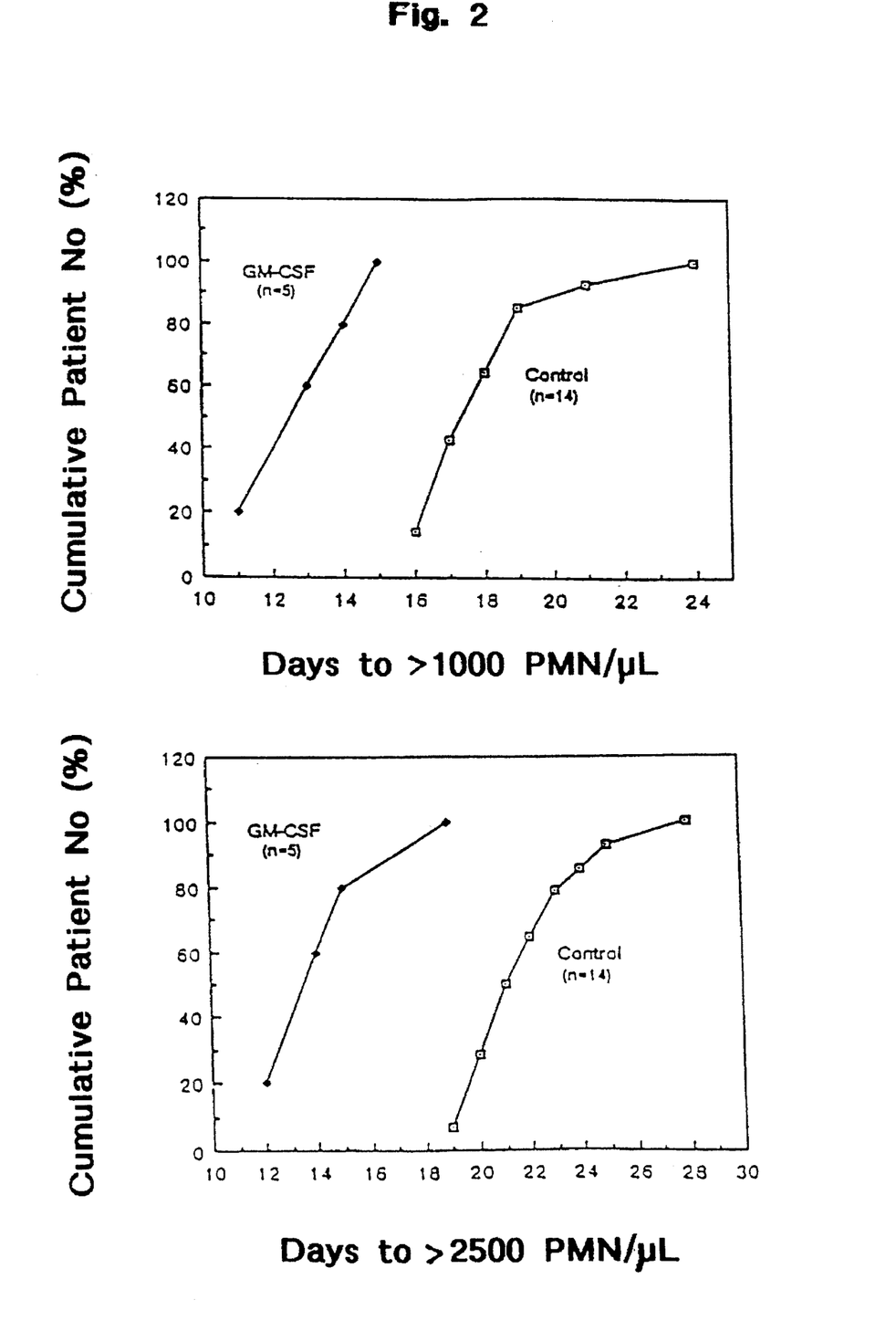
FIG. 2: distribution of neutropenia duration measured from the end of treatment (cyclophosphamide, 7 g/m$^2$ on day 0) in 14 control patients (□) and in 5 patients treated with GM-CSF (♦). Curves represent the cumulative proportions of patients reaching, within the indicated interval, more than 1000 neutrophils (upper panel) and more than 2500 neutrophils, respectively (lower panel).

Test: neutrophil count showed a more pronounced initial rise above the starting level, lasting from 2–3 days, with the nadir occurring 1–2 days earlier. The recovery phase was associated with marked leukocytosis (up to 25,000 leukocytes/µl) that gradually resolved over 3–4 days after GM-CSF discontinuation. Recovery of neutrophils to >1000/µl was achieved in 11–15 days (average 13), and to >2500/µl in 12–19 days (average 14) (FIG. 2). There were no differences documented between controls and GM-CSF treated patients in platelet counts or haemoglobin levels.

Figure 3:
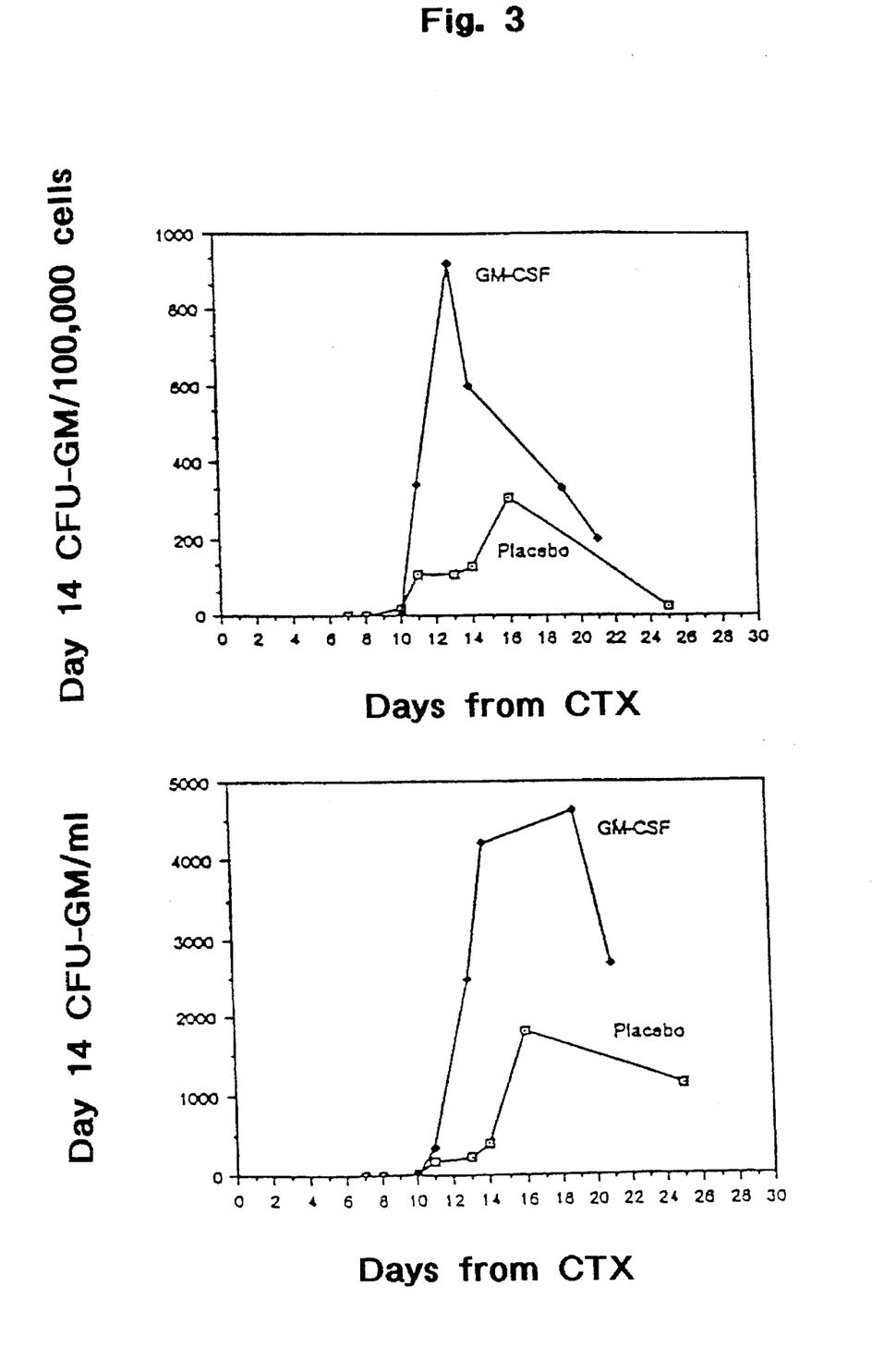
FIG. 3: effect of GM-CSF (♦) or placebo infusion (□) on circulating CFU-GM proportion (upper panel) and blood concentration (lower panel). GM-CSF was continuously infused for 10 days, starting on day 1 following cyclophosphamide (7 g/m$^2$).

Effect of GM-CSF on circulating haemopoietic progenitor cells following therapy with cyclophosphamide Using the techniques of Lanfrancone et al, supra, the number of circulating colony forming units in unperturbed conditions is approximately 40 CFU-GM/10$^6$ mononuclear cells and 40–60 CFU-GM/ml of peripheral blood. Following cyclophosphamide treatment, there was observed an approximately 100-fold higher peak value in both the proportion (CFU-GM/mononuclear cells) and the absolute number (CFU-GM/ml of peripheral blood) of colony forming units (FIG. 3). Upon addition of GM-CSF (8 µg/Kg/day from day 1 to day 10 following cyclophosphamide), CFU-GM rose by a further 3 times (peak concentration) and 5 times (peak absolute number), respectively. Of note, these high peak values were maintained for several days both in the control and in the GM-CSF treated patient. Thus, as compared with normal subjects, the total number of CFU-GM circulating in the peripheral blood during the days of stem cell expansion (area under the curve) was approximately 30-fold higher following cyclophosphamide plus GM-CSF. A further increase can be anticipated following optimal length of GM-CSF infusion. In fact recent experiments have shown that when patients are treated with GM-CSF for 14 days following cyclophosphamide, peak values as high as 85,000 CFU-GM/ml peripheral blood can be observed.

EXAMPLE 2

Figure 4:
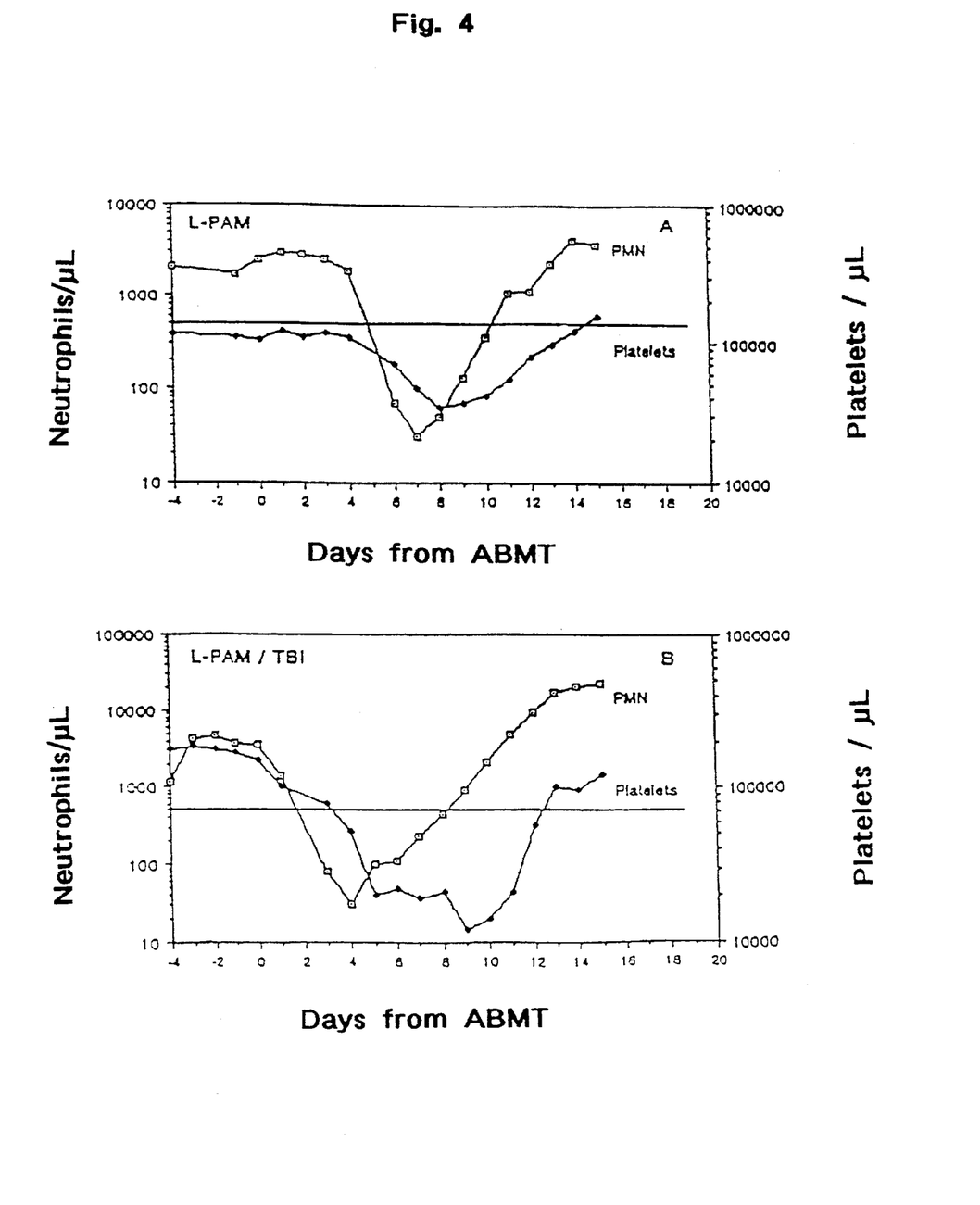
FIG. 4: granulocyte (□) and platelet (♦) counts in two patients following myeloablative treatment and autografting of bone marrow plus peripheral blood stem cells. Patient A received melphalan alone (200 mg/m$^2$); patient B total body irradiation (12.5 Gy, fractionated over 48 hours) plus melphalan (160 mg/m$^2$). Circulating stem cells were harvested twice for each patient, following prior high dose cyclophosphamide and GM-CSF infusion (see examples).

Haemotopoietic reconstitution in 2 specific patients from Example 1 is illustrated in FIG. 4.

Patient A received high dose melphalan (200 mg/m$^2$) followed by infusion of 2×10$^8$/Kg bone marrow cells and 1.8×10$^8$/Kg circulating mononuclear cells. Although she received several-fold less bone marrow and blood derived mononuclear cells than patient B, haematological toxicity followed a similar pattern. On day 6, the granulocyte count fell to less than 500/µl, remaining below this threshold for 5 days only. Platelet count never fell below 30,000/µl and no tranfusions were required. Unsupported platelet count rose to 79,000/µl on day 12 and to 120,000/µl on day 14.

Patient B had high grade non-Hodgkin's lymphoma and received 4.7×10$^8$/Kg bone marrow cells plus 8.8×10$^8$/Kg peripheral blood mononuclear cells, 24 hours after completion of high dose treatment (12.5 Gy fractionated total body irradiation and 160 mg/m$^2$ melphalan i.v.). On day 3 the granulocyte count fell below 500/µl. Starting from day 5, the patient showed a steady increase in white cell counts, reaching >500 neutrophils/µl on day 8, >1000/µl on day 10 and more than 10,000/µl on day 12. The patient's platelet count fell below 20,000/µl on day 9, requiring transfusion of one unit of platelets. Unsupported platelet count rose to >50,000/µl on day 12 and to >100,00/µl on day 13, respectively.

EXAMPLE 3

Figure 5:
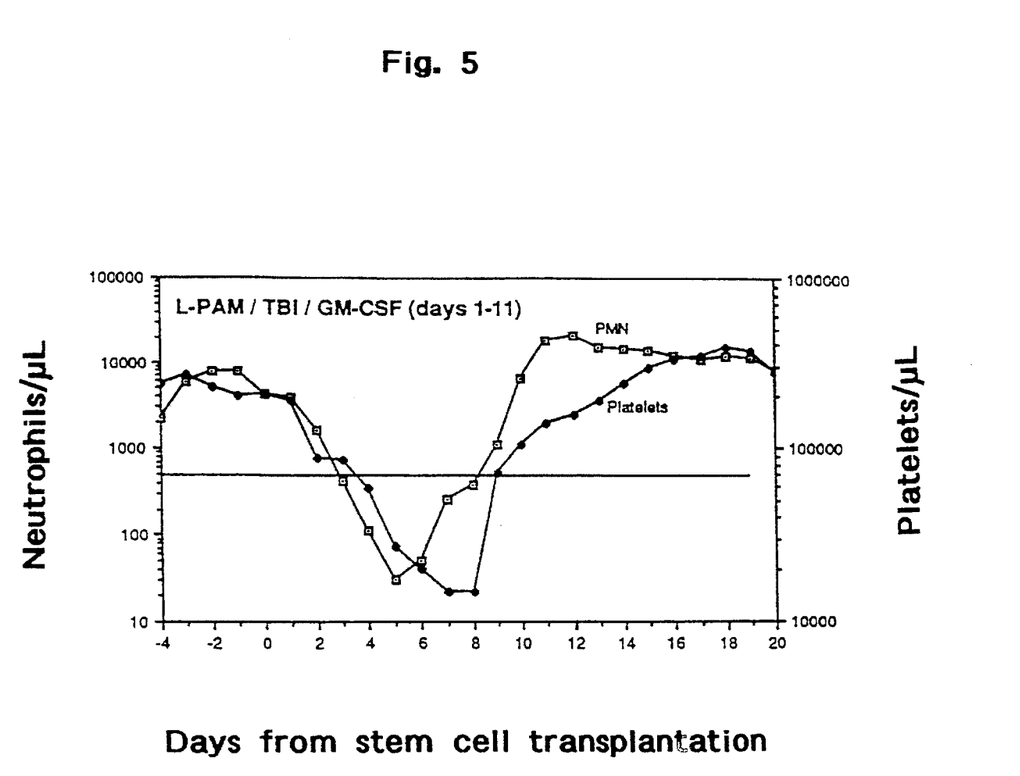
FIG. 5: Granulocyte (□) and platelet (♦) counts in one patient receiving GM-CSF infusion (8 µg/kg/day) following myeloablative treatment and autografting of bone marrow plus peripheral blood stem cells. The patient received total body irradiation (12.5 Gy, fractionated over 48 hours) plus melphalan (120 µg/m2). Circulating stem cells were harvested on days +14, +15, +16 and +17 following prior high-dose cyclophosphamide and GM-CSF infusion (8 µg/kg/day from day +1 through +14).

Haemopoietic reconstitution in one specific patient is illustrated in FIG. 5.

This patient received 7mg/m2 cyclophosphamide on day 0 and GM-CSF (8 µg/kg/day) from day +1 to day +14. Circulating mononuclear cells were collected on days +14–17 and reinfused with bone marrow cells following total body irradiation (fractionated, 12.5 Gy) and melphalan (120 mg/m2). GM-CSF (8 µg/kg/day) was infused from day +1 following autografting and discontinued on day +11 because of hyperleucocytosis (>10,000 neutrophils/µl).

I claim:

1. In a method of treating cancer in a patient comprising administering to the patient a fully myeloablative regimen of chemotherapy, radiation therapy or both, the improvement comprising carrying out, in the indicated order, the steps of a) administering to a patient having cancer a high dose of a cytotoxic but stem cell-sparing agent, b) administering to said patient a haemopoietic progenitor cell stimulating effective amount of a haemopoietic progenitor cell stimulating factor having a colony stimulating factor activity, c) when said patient's bone marrow is in an actively proliferating state, removing from the patient bone marrow and a volume of peripheral blood or leukocytes obtained from peripheral blood, and d) reinfusing into said patient bone marrow and peripheral blood or leukocytes removed in Step c), with the proviso that Steps a)–c) precede the fully myeloablative regimen and Step d) follows said fully myeloablative regimen.

2. A method according to claim 1 wherein in Step b) the haemopoietic progenitor cell stimulating effective amount of a haemopoietic progenitor cell stimulating factor having a colony stimulating factor activity is administered as a continuous intravenous infusion over a period of 10 to 14 days.

3. A method according to claim 1 wherein in Step b) the haemopoietic progenitor cell stimulating effective amount of a haemopoietic progenitor cell stimulating factor having a colony stimulating factor activity is administered beginning from 3 hours to 10 days subsequent to Step a).

4. A method according to claim 3 wherein in Step b) the haemopoietic progenitor cell stimulating effective amount of a haemopoietic progenitor cell stimulating factor having a colony stimulating factor activity is administered as a continuous intravenous infusion over a period of 10 to 14 days.

5. A method according to claim 1 further comprising the step of e) administering to said patient a haemopoietic progenitor cell stimulating effective amount of a haemopoietic progenitor cell stimulating factor having a colony stimulating factor activity for a sufficient period of time to effect myeloid recovery, Step e) being carried out subsequent to Step d).

6. A method according to claim 5 wherein Step e) is carried out identically to Step b).

7. A method according to claim 1 wherein in Step c) bone marrow and a volume of peripheral blood or leukocytes obtained from peripheral blood is removed from the patient when said patient's bone marrow is in an actively proliferating state, precursor stem cells are present in the peripheral blood and the peripheral blood cell count is above 1,000 leukocytes/µL and above 100,000 platelets/µL.

8. A method according to claim 7 wherein Step c) is carried out 12 to 21 days subsequent to Step a).

9. A method according to claim 7 wherein in Step c) bone marrow and leukocytes obtained from peripheral blood is removed from the patient when said patient's bone marrow is in an actively proliferating state, precursor stem cells are present in the peripheral blood and the peripheral blood cell count is above 1,000 leukocytes/µL and above 100,000 platelets/µL and in Step d) bone marrow and leukocytes removed in Step c) are reinfused into said patient.

10. A method according to claim 1 wherein the cytotoxic but stem cell-sparing agent administered in Step a) is cyclophosphamide or etoposide.

11. A method according to claim 10 wherein the cytotoxic but stem cell-sparing agent administered in Step a) is cyclophosphamide.

12. A method according to claim 11 wherein in Step a) cyclophosphamide is administered at a dosage of 6–7 g/m$^2$.

13. A method accoring to claim 1 for treating cancer in a patient comprising administering to the patient a fully myeloablative regimen of chemotherapy, radiation therapy or both, the improvement comprising carrying out, in the indicated order, the steps of a) administering to a patient having cancer a high dose of a cytotoxic but stem cell-sparing agent, said cytotoxic but stem cell-sparing agent being cyclophosphamide or etoposide, b) administering to said patient a haemopoietic progenitor cell stimulating effective amount of a haemopoietic progenitor cell stimulating factor having a colony stimulating factor activity as a continuous intravenous infusion over a period of 10 to 14 days beginning from 3 hours to 10 days subsequent to Step a), said haemopoietic progenitor cell stimulating factor being a GM-CSF, G-CSF or IL-3, c) when said patient's bone marrow is in an actively proliferating state, precursor stem cells are present in the peripheral blood and the peripheral blood cell count is above 1,000 leukocytes/µL and above 100,000 platelets/µL, removing from the patient bone marrow and a volume of peripheral blood or leukocytes obtained from peripheral blood, and d) reinfusing into said patient bone marrow and peripheral blood or leukocytes removed in Step c), with the proviso that Steps a)–c) precede the fully myeloablative regimen and Step d) follows said fully myeloablative regimen.

14. A method according to claim 13 further comprising the step of e) administering to said patient a haemopoietic progenitor cell stimulating effective amount of a haemopoietic progenitor cell stimulating factor having a colony stimulating factor activity for a sufficient period of time to effect myeloid recovery, Step e) being carried out subsequent to Step d).

15. A method according to claim 14 wherein Step e) is carried out identically to Step b).

16. A method according to claim 1 wherein the haemopoietic progenitor cell stimulating factor having a colony stimulating factor activity administered in Step b) is a GM-CSF, G-CSF or IL-3.

17. A method according to claim 16 wherein in Step b) the haemopoietic progenitor cell stimulating effective amount of a haemopoietic progenitor cell stimulating factor having a colony stimulating factor activity is administered beginning from 3 hours to 10 days subsequent to Step a).

18. A method according to claim 16 wherein the haemopoietic progenitor cell stimulating factor having a colony stimulating factor activity administered in Step b) is a GM-CSF.

19. A method according to claim 18 wherein the haemopoietic progenitor cell stimulating factor having a colony stimulating factor activity administered in Step b) is human GM-CSF.

20. A method according to claim 19 wherein in Step b) human GM-CSF is administered at a dosage of 6–24 µg/Kg body weight/day.

21. A method according to claim 20 wherein in Step b) human GM-CSF is administered at a dosage of 8 µg/Kg body weight/day.

22. A method according to claim 20 wherein in Step b) human GM-CSF is, beginning from 3 hours to 10 days subsequent to Step a), administered as a continuous intravenous infusion over a period of 10 to 14 days at a dosage of 6–24 µg/Kg body weight/day.

23. In a method of treating cancer in a patient comprising administering to the patient a fully myeloablative regimen of chemotherapy, radiation therapy or both, the improvement comprising carrying out, in the indicated order, the steps of a) administering to a patient having cancer a high dose of a cytotoxic but stem cell-sparing agent, b) administering to said patient a haemopoietic progenitor cell stimulating effective amount of a haemopoietic progenitor cell stimulating factor having a colony stimulating factor activity, c) when precursor stem cells are present in the peripheral blood, removing from the patient a volume of peripheral blood or leukocytes obtained from peripheral blood, and d) reinfusing into said patient peripheral blood or leukocytes removed in Step c), with the proviso that Steps a)–c) precede the fully myeloablative regimen and Step d) follows said fully myeloablative regimen.

24. A method according to claim 23 wherein the haemopoietic progenitor cell stimulating factor having a colony stimulating factor activity administered in Step b) is a GM-CSF or IL-3.

* * * * *